United States Patent
Mimura et al.

(12)

(10) Patent No.: US 6,197,998 B1
(45) Date of Patent: Mar. 6, 2001

(54) PROCESS FOR PRODUCING N-GLYCYLTYROSINE AND ITS CRYSTAL STRUCTURE

(75) Inventors: Takashi Mimura, Tokyo; Eiichiro Imai, Sakai; Takahiro Imai, Sakai; Takehiro Ogasa, Sakai; Masaji Kasai, Fujisawa, all of (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/289,737

(22) Filed: Apr. 12, 1999

(30) Foreign Application Priority Data

Apr. 14, 1998 (JP) .................................... 10-103100

(51) Int. Cl.⁷ ................................. C07C 229/00
(52) U.S. Cl. ........................... 562/444; 562/445; 562/450
(58) Field of Search ................... 562/445, 448, 562/444, 450

(56) References Cited

U.S. PATENT DOCUMENTS 5,780,677   7/1998   Amatsu et al. ..................... 562/561

OTHER PUBLICATIONS

Berichte der Deutschen Chemischen Gesellschaft, pp. 2486–2511 (1904).
Journal of Organic Chemistry, 18, pp. 127–132 (1953).
Journal of Organic Chemistry, 18, pp. 1546–1553 (1953).
Crystal Structure Communication, 1, pp. 301–304 (1972).
G. C. Barrett and D. T. Elmore, "Amino Acids and Peptides." Cambridge Univ. Press; pp. 48–77, 1998.*

* cited by examiner

*Primary Examiner*—Paul J. Killos
(74) *Attorney, Agent, or Firm*—Fitzpatrick, Cella, Harper & Scinto

(57) ABSTRACT

Provided is a process for efficiently producing N-glycyltyrosine of high purity represented by the following formula:

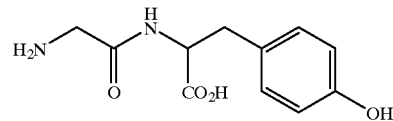

a salt thereof, or a solvate thereof, which comprises adding dropwise to an aqueous suspension of tyrosine or a salt thereof 2 equivalents or more of a haloacetyl halide and an aqueous solution of an inorganic base simultaneously in the presence or absence of an organic solvent, and subjecting the resulting N-haloacetyltyrosine to a reaction with an ammonium ion. Also provided are N-glycyl-L-tyrosine dehydrate having the crystal structures showing specific diffraction patterns in X-ray powder diffraction and processes for producing the same which are characterized by comprising crystallizing the dihydrate from an ethanol-water mixed solvent or water.

18 Claims, No Drawings

PROCESS FOR PRODUCING N-GLYCYLTYROSINE AND ITS CRYSTAL STRUCTURE

BACKGROUND OF THE INVENTION

The present invention relates to a process for efficiently producing N-glycyltyrosine including N-glycyl-L-tyrosine dehydrate, which is one of the dipeptides useful as an ingredient of infusions. The invention also relates to N-glycyl-L-tyrosine dihydrate having specific crystal structures and processes for producing the same.

Amino acids and dipeptides thereof have been conventionally used as ingredients of infusions. N-Glycyl-L-tyrosine is a derivative prepared for the purpose of improving the solubility of L-tyrosine, which has very low water-solubility.

A process for producing N-glycyl-L-tyrosine is disclosed in Berichte der Deutschen Chemischen Gesellschaft, p. 2486 (1904). In the process, L-tyrosine is subjected to a reaction with 1.1 equivalents of chloroacetyl chloride and an aqueous solution of sodium hydroxide to obtain N-chloroacetyl-L-tyrosine, which is then made to react with aqueous ammonia to prepare N-glycyl-L-tyrosine. This process gives N-chloroacetyl-L-tyrosine, which is an intermediate for the synthesis of N-glycyl-L-tyrosine, in a 50% yield. The above literature also discloses a process in which L-tyrosine ethyl ester is made to react with 1.0 equivalent of chloroacetyl chloride to form N-chloroacetyl-L-tyrosine ethyl ester, which is then hydrolyzed to prepare N-chloroacetyl-L-tyrosine. In this process, the overall yield of N-chloroacetyl-L-tyrosine based on L-tyrosine ethyl ester is 91%, and that based on L-tyrosine is 77% as the yield in the step of conversion into ethyl ester from L-tyrosine is 85%. The process for producing N-glycyl-L-tyrosine via L-tyrosine ethyl ester is thus advantageous in respect of yield over the process in which L-tyrosine is directly chloroacetylated. However, when applied to the production on an industrial scale, the former process which requires the steps of esterification and hydrolysis is inefficient compared with the latter process requiring a smaller number of steps.

Another process for producing N-haloacetyl-L-tyrosine by direct haloacetylation of L-tyrosine is disclosed in Journal of Organic Chemistry, 18, 127(1953) and ibid., 18, 1546(1953). In this process, N-haloacetyl-L-tyrosine is produced by a reaction of L-tyrosine with 1-2 equivalents of chloroacetyl chloride in ethyl acetate under reflux. This reaction must be carried out under severe conditions. Further, the yield of the reaction product is 59% and thus the process is not satisfactory in respect of efficiency.

The crystal structure of N-glycyl-L-tyrosine dehydrate is disclosed in Crystal Structure Communication, 1, 301 (1972).

Under the circumstances, a one-step process for producing N-haloacetyltyrosine from tyrosine in high yields is desired for the production of N-glycyltyrosine using N-haloacetyltyrosine as an intermediate.

An object of the present invention is to efficiently produce N-haloacetyltyrosine and to efficiently produce N-glycyltyrosine by ammonolysis of N-haloacetyltyrosine using ammonia, if necessary in the presence of inorganic salts. Another object of the invention is to provide a process for producing N-glycyl-L-tyrosine dihydrate having specific crystal structures suitable for use as an ingredient of pharmaceutical compositions.

SUMMARY OF THE INVENTION

The present invention relates to a process for producing N-glycyltyrosine represented by formula (III):

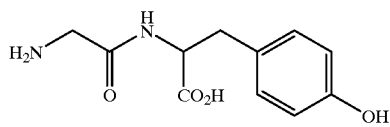

a salt thereof, or a solvate thereof, which comprises adding dropwise to an aqueous suspension of tyrosine or a salt thereof 2 equivalents or more of a haloacetyl halide represented by formula (I):

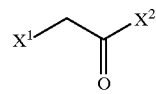

(wherein $X^1$ and $X^2$, which may be the same or different, each represent chlorine, bromine or iodine) and an aqueous solution of an inorganic base simultaneously in the presence or absence of an organic solvent, to form N-haloacetyltyrosine represented by formula (II):

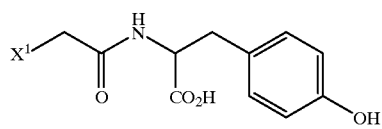

(wherein $X^1$ has the same meaning as defined above) (haloacetylation), and subjecting the resulting N-haloacetyltyrosine to a reaction with an ammonium ion.

In this process, the reaction temperature and pH of the reaction mixture in the step of haloacetylation of tyrosine are preferably maintained at −20 to 30° C. and at pH 8 to 14, respectively.

The invention relates to a process for producing N-haloacetyltyrosine represented by the above formula (II), a salt thereof, or a solvate thereof, which comprises adding dropwise to an aqueous suspension of tyrosine or a salt thereof 2 equivalents or more of a haloacetyl halide represented by the above formula (I) and an aqueous solution of an inorganic base simultaneously in the presence or absence of an organic solvent.

In this process, the reaction temperature and pH of the reaction mixture are preferably maintained at −20 to 30° C. and at pH 8 to 14, respectively.

The invention also relates to a process for producing N-glycyl-L-tyrosine dihydrate having the crystal structure giving the following diffraction pattern of the diffraction angle 2θ° and the relative diffraction intensity shown in parentheses in terms of % I/I₀ in X-ray powder diffraction within the limit of experimental errors: 7.96 (22), 15.20 (26), 15.86 (16), 18.92 (26), 19.96 (14), 21.16 (54), 21.52 (24), 23.08 (17), 23.84 (100), 26.44 (17), 27.08 (22), 28.88 (20), 31.64 (20), 33.72 (9), 35.28 (11), which is characterized by comprising crystallizing the dehydrate from a water-ethanol mixed solvent (ethanol content:10–99 vol %)(hereinafter, the above crystal structure is referred to as crystal structure A).

Further, the invention relates to N-glycyl-L-tyrosine dehydrate having the crystal structure giving the following diffraction pattern of the diffraction angle 2θ° and the relative diffraction intensity shown in parentheses in terms of % I/I$_0$ in X-ray powder diffraction within the limit of experimental errors: 7.36 (16), 9.48 (17), 10.12 (23), 11.24 (100), 13.80 (14), 14.72 (19), 15.32 (58), 22.16 (59), 22.56 (37), 23.08 (56), 25.56 (31), 26.84 (28), 28.76 (39), 29.72 (38), 33.12 (22), 34.16 (23), and to a process for producing the same, which is characterized by comprising crystallizing the same from water (hereinafter, the above crystal structure is referred to as crystal structure B).

DETAILED DESCRIPTION OF THE INVENTION

Tyrosine to be used in the production of N-glycyltyrosine may be in any of D-form, L-form and DL-form. In order to obtain N-glycyl-L-tyrosine, which is a dipeptide useful as an ingredient of infusions, L-tyrosine is used. Tyrosine may be used as such or in the form of a salt. Preferred salts include a disodium salt and a monohydrochloride.

Preferred organic solvents for the production of N-haloacetyltyrosine are aromatic hydrocarbons, halogenated hydrocarbons, fatty acid esters, cyclic or acyclic ether compounds, ketones, and mixtures thereof. Preferred inorganic bases to be added dropwise together with a haloacetyl halide are lithium hydroxide, sodium hydroxide, potassium hydroxide, and mixtures thereof. The haloacetyl halide is used in the reaction in an amount of 2 equivalents or more, preferably 2 to 6 equivalents based on tyrosine. The reaction temperature is preferably −20 to 30° C., more preferably −10 to 10° C. The reaction mixture is preferably kept at pH 8 to 14, more preferably at pH 11 to 13.

Chloroacetyl chloride is one of the preferred haloacetyl halides.

The haloacetylation of tyrosine is carried out in the presence or absence of an organic solvent. As the organic solvent, aromatic hydrocarbons (e.g., benzene, toluene and xylene), halogenated hydrocarbons (e.g., chloroform, methylene chloride and 1,2-dichloroethane), fatty acid esters (e.g., ethyl acetate and isopropyl acetate), cyclic or acyclic ether compounds (e.g., tetrahydrofuran and diethyl ether) and ketones (e.g. acetone and ethyl methyl ketone) can be used alone or in combination in an amount of 0.5 to 30 times, preferably 0.5 to 5 times, the amount of tyrosine (weight/weight). Water is used as a solvent in an amount of 1 to 30 times, preferably 3 to 5 times, the amount of tyrosine (weight/weight). The reaction is carried out at a temperature of −20 to 30° C., preferably −10 to 10° C., at pH 8 to 14, preferably 11 to 13. After the completion of the reaction, the pH of the water layer is adjusted to below 3, preferably 1 to 2, to cause crystallization. The resulting crystals are isolated by filtration, whereby N-haloacetyltyrosine is obtained in high yields. This process is advantageous over the previous methods in that N-haloacetyltyrosine can be produced from tyrosine by one step in high yields. Needless to say, the reaction product retains the optical purity of tyrosine used as a starting material.

Production of N-glycyltyrosine from N-haloacetyltyrosine can be carried out according to the procedures described in Berichte der Deutschen Chemischen Gesellschaft, p. 2486 (1904) and Journal of Organic Chemistry, 18, 127 (1953).

Ammonium ion sources useful for the ammonolysis include aqueous ammonia, ammonia, ammonium hydrogencarbonate, ammonium carbonate, etc., which are used in an amount of 10 to 100 equivalents, preferably 20 to 100 equivalents.

The desired compounds produced by the above process can be purified by purification methods conventionally used in synthetic organic chemistry, for example, recrystallization, chromatography or resin treatment. Not only N-glycyltyrosine or N-haloacetyltyrosine in a free state but also N-glycyltyrosine or N-haloacetyltyrosine in the form of a salt or a solvate such as a hydrate can be obtained by conventional methods in synthetic organic chemistry. Crystallization from a water-ethanol mixed solvent (ethanol content: 10–99 vol %, preferably 15–50 vol %) in an amount of 8 to 30 times per weight, preferably 9 to 15 times, the amount of N-glycyl-L-tyrosine at 0 to 5° C. for one minute to 100 hours gives with high reproducibility N-glycyl-L-tyrosine dehydrate having the crystal structure (crystal structure A) showing specific spectra in crystal structure analyses such as IR, X-ray powder diffraction and TG-DTA (thermogravimetric and differential thermal analysis). Crystallization from water in an amount of 5 to 30 times per weight, preferably 5 to 10 times, the amount of N-glycyl-L-tyrosine at 0 to 5° C. for more than 20 hours, preferably 20 to 100 hours, gives with high reproducibility N-glycyl-L-tyrosine dihydrate having the crystal structure (crystal structure B) showing specific spectra different from those observed by the use of a water-ethanol mixed solvent in crystal structure analyses such as IR, X-ray powder diffraction and TG-DTA (thermogravimetric and differential thermal analysis).

Certain embodiments of the invention are illustrated in the following Examples and Reference Example.

EXAMPLE 1

Production of N-chloroacetyl-L-tyrosine

L-Tyrosine (600 g, 3.31 mol) was suspended in a mixture of 1200 ml of distilled water, 900 ml of a 4 N aqueous solution of sodium hydroxide and 600 ml of toluene, and the suspension was cooled to −5 to 0° C. To this suspension were simultaneously added dropwise a mixture of 792 ml (9.93 mol) of chloroacetyl chloride and 792 ml of toluene and a 10 N aqueous solution of sodium hydroxide, while maintaining the reaction mixture at pH 12 to 12.6 and at a temperature below 5° C. After the addition was completed, the resulting mixture was adjusted to pH 8.5 with concentrated hydrochloric acid, followed by separation of the water layer. The conversion of N-chloroacetyl-L-tyrosine in the water layer was 92.6%. The water layer was adjusted to pH 1.5 with concentrated hydrochloric acid, and the deposited crystals were isolated by filtration and then suspended in 600 ml of distilled water. The suspension was ice-cooled and the deposited crystals were isolated by filtration to give 707 g (2.74 mol, 82.8%) of the desired compound.

Melting point: 154° C. (decomposition)

Elemental analysis: Found: C, 51.27; H, 4.74; N, 5.39%. Calcd. for $C_{11}H_{12}ClNO_4$: C, 51.27; H, 4.69; N, 5.44%.

IR absorption spectrum (KBr, cm$^{-1}$): 3290, 1707, 1659, 1556, 1516, 1452, 1231, 1105

$^1$H-NMR spectrum (DMSO-d$_6$, δ ppm): 2.80 (dd, J=8.6, 3.9 Hz, 1H), 2.95 (dd, J=5.0, 13.9 Hz, 1H), 4.06 (s, 2H), 4.37 (ddd, J=5.0, 8.2, 8.3 Hz, 1H), 6.65 (d, J=8.4 Hz, 2H), 6.99 (d, J=8.4 Hz, 2H), 8.40 (d, J=7.9 Hz, 1H), 9.21 (br, 1H)

REFERENCE EXAMPLE 1

Comparison of an amount (expressed in equivalent) of chloroacetyl chloride in the production of N-chloroacetyl-L-tyrosine L-Tyrosine (10 g, 55.2 mmol) was suspended in a mixture of 15 ml of a 4 N aqueous solution of sodium hydroxide and 10 ml of toluene, and the suspension was cooled to −5 to 0°

C. To this suspension were simultaneously added dropwise a 1:1 mixture of chloroacetyl chloride and toluene and a 4 N aqueous solution of sodium hydroxide, while maintaining the reaction mixture at pH 12 to 12.5 and at a temperature below 5° C. After the addition was completed, the water layer was separated and the conversion of N-chloroacetyl-L-tyrosine in the water layer was measured. The result is shown in the following table.

| Amount of chloro-acetyl chloride (eq.) | Conversion of N-chloroacetyl-L-tyrosine (%) | Residual rate of L-tyrosine (%) |
|---|---|---|
| 1.0 | 64.2 | 35.2 |
| 2.0 | 85.8 | 14.1 |
| 3.0 | 89.9 | 9.7 |
| 4.0 | 95.4 | 4.3 |

EXAMPLE 2

Production of N-glycyl-L-tyrosine dehydrate and preparation of crystals thereof with crystal structure A Ammonium hydrogencarbonate (1289 g) was dissolved in a mixture of 4000 ml of 28% aqueous ammonia and 1000 ml of distilled water at 35° C. To the solution were added 700 g (2.72 mol) of N-chloroacetyl-L-tyrosine and 700 ml of distilled water, followed by stirring at 40° C. for 5 hours. The reaction mixture was concentrated under reduced pressure to remove excess ammonia and then adjusted to pH 5.5 with concentrated hydrochloric acid at 45° C., followed by gradual cooling. After crystals were deposited, the mixture was ice-cooled and the crystals were isolated by filtration to give 600 g (489 g on anhydrous basis, 2.05 mol, 75.4%) of crude crystals of N-glycyl-L-tyrosine.

The obtained crude crystals (589 g, 480 g on anhydrous basis, 2.01 mol) were dissolved in 9600 ml of distilled water at 40° C. The solution was passed through a column of a weakly basic resin (WA-30 OH, 960 ml) and the fractions containing the desired compound were collected. The combined aqueous solution was concentrated under reduced pressure to 2667 ml, and 1333 ml of ethanol was added thereto, followed by recrystallization. The resulting crystals were dried under reduced pressure to give 482 g (1.76 mol, 87.5%) of the desired compound.

Melting point: 277° C. (decomposition)

Elemental analysis: Found: C, 48.27; H, 6.51; N, 10.21%. Calcd. for $C_{11}H_{14}N_2O_4 \cdot 2H_2O$: C, 48.17; H, 6.61; N, 10.21%.

IR absorption spectrum (KBr, $cm^{-1}$): 3361, 1668, 1537, 1458, 1421, 1389, 1240, 1148, 1115

$^1$H-NMR spectrum (DMSO-$d_6$, δ ppm): 2.75 (dd, J=7.4, 13.6 Hz, 1H), 2.96 (dd, J=4.3, 13.6 Hz, 1H), 3.29 (d, J=16.4 Hz, 1H), 3.43 (d, J=16.4 Hz, 1H), 4.22 (m, 1H), 6.63 (d, J=7.3 Hz, 2H), 6.96 (d, J=7.7 Hz, 2H), 8.21 (m, 1H)

X-ray powder diffraction [diffraction angle, 2θ°; relative intensity, % $I/I_0$ (shown in parentheses)]: 7.96 (22), 15.20 (26), 15.86 (16), 18.92 (26), 19.96 (14), 21.16 (54), 21.52 (24), 23.08 (17), 23.84 (100), 26.44 (17), 27.08 (22), 28.88 (20), 31.64 (20), 33.72 (9), 35.28 (11)

EXAMPLE 3

Preparation of crystals of N-glycyl-L-tyrosine dihydrate with crystal structure B N-Glycyl-L-tyrosine dihydrate (118.5 g, 100.0 g on anhydrous basis, 0.432 mol) obtained in Example 2 was suspended in 600 ml of distilled water at 25° C., followed by crystallization at 5° C. for 46 hours. The resulting crystals were dried under reduced pressure to give 106.4 g (0.388 mol, 89.8%) of the desired compound.

Melting point: 277° C. (decomposition)

IR absorption spectrum (KBr, $cm^{-1}$): 3327, 1653, 1545, 1516, 1462, 1445, 1414, 1379, 1253, 1107

X-ray powder diffraction [diffraction angle, 2θ°; relative intensity, % $I/I_0$ (shown in parentheses)]: 7.36 (16), 9.48 (17), 10.12 (23), 11.24 (100), 13.80 (14), 14.72 (19), 15.32 (58), 22.16 (59), 22.56 (37), 23.08 (56), 25.56 (31), 26.84 (28), 28.76 (39), 29.72 (38), 33.12 (22), 34.16 (23)

What is claimed is:

1. A process for producing N-glycyltyrosine represented by formula (III):

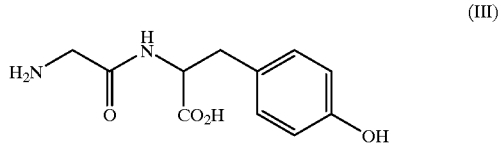

a salt thereof, or a solvate thereof, which comprises adding dropwise to an aqueous suspension of tyrosine or a salt thereof 2 equivalents or more of a haloacetyl halide represented by formula (I):

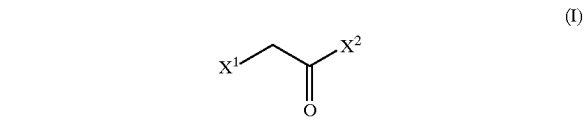

(wherein $X^1$ and $X^2$, which may be the same or different, each represent chlorine, bromine or iodine) and an aqueous solution of an inorganic base simultaneously in the presence or absence of an organic solvent, to form N-haloacetyltyrosine represented by formula (II):

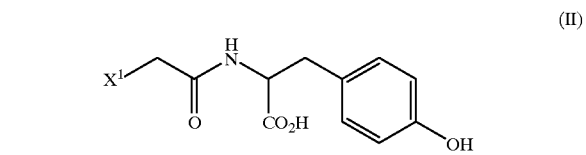

(wherein $X^1$ has the same meaning as defined above) (haloacetylation), and subjecting the resulting N-haloacetyltyrosine to a reaction with an ammonium ion.

2. The process according to claim 1, wherein the reaction temperature and pH of the reaction mixture in the step of haloacetylation of tyrosine are maintained at −20 to 30° C. and at pH 8 to 14, respectively.

3. The process according to claim 1 or 2, wherein said tyrosine is L-tyrosine, said N-haloacetyltyrosine is N-haloacetyl-L-tyrosine, and said N-glycyltyrosine is N-glycyl-L-tyrosine.

4. The process according to claim 3, wherein said solvate of N-glycyl-L-tyrosine is N-glycyl-L-tyrosine dihydrate.

5. The process according to claim 1 or 2, wherein said organic solvent is selected from the group consisting of an aromatic hydrocarbon, a halogenated hydrocarbon, a fatty acid ester, a cyclic or acyclic ether compound, a ketone, and a mixture thereof.

6. The process according to claim 1 or 2, wherein said inorganic base is selected from the group consisting of lithium hydroxide, sodium hydroxide, potassium hydroxide, and a mixture thereof.

7. The process according to claim 1 or 2, wherein said haloacetyl halide is added dropwise in an amount of 2 to 6 equivalents simultaneously with the aqueous solution of the inorganic base, while maintaining the reaction mixture at a temperature of −20 to 30° C. and at pH 8 to 14.

8. The process according to claim 7, wherein pH is 11 to 13.

9. The process according to claim 8, wherein said haloacetyl halide is chloroacetyl chloride.

10. A process for producing N-haloacetyltyrosine represented by formula (II):

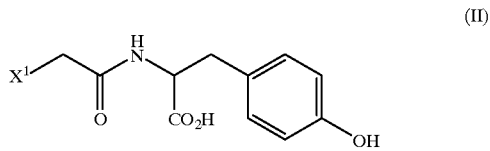

(II)

(wherein $X^1$ has the same meaning as defined above), a salt thereof, or a solvate thereof, which comprises adding dropwise to an aqueous suspension of tyrosine or a salt thereof 2 equivalents or more of a haloacetyl halide represented by formula (I):

(I)

(wherein $X^1$ and $X^2$ have the same meanings as defined above) and an aqueous solution of an inorganic base simultaneously in the presence or absence of an organic solvent.

11. The process according to claim 10, wherein the reaction temperature and pH of the reaction mixture are maintained at −20 to 30° C. and at pH 8 to 14, respectively.

12. The process according to claim 10 or 11, wherein said tyrosine is L-tyrosine, said N-haloacetyltyrosine is N-haloacetyl-L-tyrosine.

13. The process according to claim 10 or 11, wherein said organic solvent is selected from the group consisting of an aromatic hydrocarbon, a halogenated hydrocarbon, a fatty acid ester, a cyclic or acyclic ether compound, a ketone, and a mixture thereof.

14. The process according to claim 10 or 11, wherein said inorganic base is selected from the group consisting of lithium hydroxide, sodium hydroxide, potassium hydroxide, and a mixture thereof.

15. The process according to claim 10 or 11, wherein said haloacetyl halide is added dropwise in an amount of 2 to 6 equivalents simultaneously with the aqueous solution of the inorganic base, while maintaining the reaction mixture at a temperature of −20 to 30° C. and at pH 8 to 14.

16. The process according to claim 15, wherein pH is 11 to 13.

17. The process according to claim 16, wherein said haloacetyl halide is chloroacetyl chloride.

18. A process for producing N-glycyl-L-tyrosine dehydrate having the crystal structure giving the following diffraction pattern of the diffraction angle 2θ° and the relative diffraction intensity shown in parentheses in terms of % $I/I_0$ in X-ray powder diffraction within the limit of experimental errors: 7.96 (22), 15.20 (26), 15.86 (16), 18.92 (26), 19.96 (14), 21.16 (54), 21.52 (24), 23.08 (17), 23.84 (100), 26.44 (17), 27.08 (22), 28.88 (20), 31.64 (20), 33.72 (9), 35.28 (11), which is characterized by comprising crystallizing the dihydrate from a water-ethanol mixed solvent (ethanol content: 10–99 vol %).

* * * * *

UNITED STATES PATENT AND TRADEMARK OFFICE
CERTIFICATE OF CORRECTION

PATENT NO. : 6,197,998 B1  
DATED : March 6, 2001  
INVENTOR(S) : Takashi Mimura et al.

Page 1 of 1

It is certified that error appears in the above-identified patent and that said Letters Patent is hereby corrected as shown below:

<u>Title page,</u>  
Item [57] ABSTRACT,  
Line 10, "dehydrate" should read -- dihydrate --.

<u>Column 1,</u>  
Line 7, "dehydrate," should read -- dihydrate, --; and  
Line 49, "dehydrate" should read -- dihydrate --.

<u>Column 2,</u>  
Line 60, "dehydrate" should read -- dihydrate --; and  
Line 65, "dehydrate" should read -- dihydrate --.

<u>Column 4,</u>  
Line 12, "dehydrate" should read -- dihydrate --.

<u>Column 5,</u>  
Line 21, "dehydrate" should read -- dihydrate --.

<u>Column 8,</u>  
Line 24, "dehy-" should read -- dihy- --.

Signed and Sealed this

Twenty-sixth Day of March, 2002

*Attest:*

JAMES E. ROGAN  
*Director of the United States Patent and Trademark Office*

*Attesting Officer*